United States Patent
Liebeskind et al.

(10) Patent No.: US 9,833,598 B2
(45) Date of Patent: Dec. 5, 2017

(54) VENOUS MODULATION OF COLLATERAL PERFUSION OF CEREBRAL ISCHEMIA

(71) Applicant: The Regents of the University of California, Oakland, CA (US)

(72) Inventors: David S. Liebeskind, Los Angeles, CA (US); Osvaldas Pranevicius, New York, NY (US); Mindaugas Pranevicius, Forest Hills, NY (US)

(73) Assignee: The Regents of the University of California, Oakland, CA (US)

( * ) Notice: Subject to any disclaimer, the term of this patent is extended or adjusted under 35 U.S.C. 154(b) by 316 days.

(21) Appl. No.: 14/220,020

(22) Filed: Mar. 19, 2014

(65) Prior Publication Data

US 2014/0207170 A1   Jul. 24, 2014

Related U.S. Application Data

(63) Continuation of application No. 12/740,623, filed as application No. PCT/US2008/082161 on Oct. 31, 2008.

(Continued)

(51) Int. Cl.
*A61M 29/00* (2006.01)
*A61M 25/10* (2013.01)
(Continued)

(52) U.S. Cl.
CPC ... *A61M 25/10181* (2013.11); *A61B 17/1204* (2013.01); *A61B 17/1322* (2013.01);
(Continued)

(58) Field of Classification Search
USPC .................. 600/194, 419; 606/194, 191, 201
See application file for complete search history.

(56) References Cited

U.S. PATENT DOCUMENTS

| | | | |
|---|---|---|---|
| 4,625,277 A | 11/1986 | Pearce et al. | |
| 6,044,845 A * | 4/2000 | Lewis | A61M 25/104 |
| | | | 128/898 |

(Continued)

OTHER PUBLICATIONS

Cerebral venous steal: blood flow diversion with increased tissue pressure Mindaugas Pranevicius, Osvaldas Pranevicius Neurosurgery. Nov. 2002; 51(5): 1267-1274. (Pranevicius).*

(Continued)

*Primary Examiner* — Christian Jang
*Assistant Examiner* — Mitchell E Alter
(74) *Attorney, Agent, or Firm* — Fenwick & West LLP (57) ABSTRACT

A patient in whom blood diversion due to cerebral venous steal is present, and abolishment of the cerebral venous steal is indicated, is treated by increasing the cerebral venous pressure in the patient. This increase in cerebral venous pressure restores the collapsed cerebral vasculature, thereby increasing cerebral blood flow. The increase in cerebral venous pressure may be achieved using an occluding catheter in the superior vena cava or the internal jugular veins, using external compression of the cervical veins, or any other suitable mechanism. The occlusion may be controlled precisely during treatment, possibly as a function of cerebral blood flow, and after treatment the patient may experience a persistent effect because the cerebral vasculature is no longer collapsed.

15 Claims, 4 Drawing Sheets

Related U.S. Application Data (60) Provisional application No. 60/984,372, filed on Oct. 31, 2007.

(51) Int. Cl.
   *A61B 17/12* (2006.01)
   *A61B 17/132* (2006.01)

(52) U.S. Cl.
   CPC ........ *A61M 25/10* (2013.01); *A61M 25/1018* (2013.01); *A61M 2025/1052* (2013.01)

(56) References Cited

U.S. PATENT DOCUMENTS

| | | | | |
|---|---|---|---|---|
| 6,383,172 | B1* | 5/2002 | Barbut | A61M 1/3653 128/898 |
| 6,848,448 | B1* | 2/2005 | St. Germain | A61B 5/0215 128/898 |
| 6,942,686 | B1 | 9/2005 | Barbut et al. | |
| 7,118,534 | B2* | 10/2006 | Ward | A61B 5/022 600/485 |
| 2007/0135793 | A1* | 6/2007 | Barbut | A61B 5/0215 604/509 |

OTHER PUBLICATIONS

"The Use of Transcranial Doppler Ultrasonography as a 'Cerebral Stethoscope' for the Assessment and Treatment of Acute Stroke," Syme, Journal of Royal College of Physicians of Edinburgh 2006; 36:17-28 (Syme).

United States Office Action, U.S. Appl. No. 12/740,623, dated Jan. 29, 2013, 8 pages.

United States Office Action, U.S. Appl. No. 12/740,623, dated Nov. 20, 2013, 11 pages.

Canadian Office Action, Canadian Application No. 2,703,845, dated Jan. 10, 2014, 2 pages.

Canadian Office Action, Canadian Application No. 2,703,845, dated Mar. 14, 2012, 2 pages.

PCT International Search Report and Written Opinion, PCT Application No. PCT/US08/82161, dated Jan. 21, 2009, 8 pages.

* cited by examiner

VENOUS MODULATION OF COLLATERAL PERFUSION OF CEREBRAL ISCHEMIA

CROSS REFERENCE TO RELATED APPLICATIONS

This application is a continuation of U.S. patent application Ser. No. 12/740,623, filed Apr. 29, 2010, (pending) which is the National Stage of International Patent Application No. PCT/US2008/082161, filed Oct. 31, 2008, which claims priority to U.S. Provisional Patent Application No. 60/984,372, filed Oct. 31, 2007. The contents of these prior applications are hereby incorporated by reference in their entirety for all purposes.

STATEMENT REGARDING FEDERALLY SPONSORED RESEARCH OR DEVELOPMENT

This invention was made with Government support under Grant No. NS054084 awarded by the National Institutes of Health. The Government has certain rights in the invention.

BACKGROUND

This invention relates generally to medical devices and methods, and more particularly, to catheters, systems, kits, and methods for treating cerebral ischemia, such as acute or chronic ischemia associated with stroke.

Stroke remains a devastating and common clinical disorder, yet treatment options are limited. In recent years, the field of cardiology has witnessed remarkable advances in the prevention and treatment of ischemic heart disease. However, cerebral ischemia has eluded the stroke research community's fervent efforts to reverse or even limit the degree of neurologic injury that develops within only minutes or hours of stroke onset yet may result in lifelong disability.

Much attention has been devoted to the ischemic cascade, or sequence of cellular and molecular events that occur in the brain when arterial blood flow is diminished. Traditional descriptions of the ischemic cascade in stroke focus on organ-specific aspects of pathophysiology such as deleterious events in brain tissue, neglecting critical vascular elements such as hemodynamic compensation, endothelial ischemia, or blood-brain barrier permeability that accompany early phases of acute ischemic stroke. Recognition of the neurovascular unit has recently shifted focus to the complex interaction between vascular elements and specific pathophysiologic events in the ischemic brain. Increasing use of advanced noninvasive imaging modalities and endovascular procedures for acute ischemic stroke has also provided a wealth of information regarding the critical role of collateral perfusion.

The emphasis on vascular aspects of acute ischemic stroke prevails in the clinical realm. Almost a dozen years after the introduction of thrombolysis for acute ischemic stroke, the only advance in treatment has been the US Food and Drug Administration (FDA) clearance of the Merci device (Concentric Medical, Mountain View, Calif.) for mechanical thrombectomy. As a result, the only approved means to treat stroke is to remove the clot obstructing an artery feeding the brain with essential oxygen and nutrients. Unfortunately, this approach can only be used in a subset of cases.

Recent investigational strategies have attempted to improve upon this approach with newer and potentially safer clot-busting approaches. Novel thrombolytic and antithrombotic drugs, alternative endovascular thrombectomy devices, and even noninvasive use of ultrasound have been proposed to enhance recanalization. Although recanalization is an important facet of acute stroke therapy, numerous limitations abound. Persistent arterial occlusion occurs in a substantial subset of cases, and recanalization is not tantamount to reperfusion, as distal emboli may ensue. Rethrombosis may occur in one of every three thrombolysis cases. Reperfusion of the proximal artery may also not herald improved neurologic outcome, as some regions of downstream ischemia may not be vulnerable due to established compensation via collateral perfusion. Proximal recanalization may also hasten hemorrhagic transformation or bleeding into areas of severe ischemic injury. Neuroprotective strategies have attempted to circumvent this aspect by conducting clinical trials that consider ischemia and hemorrhage. However, effective delivery of neuroprotective agents is also dependent on collateral perfusion, underscoring the emphasis on vascular pathophysiology.

The introduction of devices to treat acute ischemic stroke has also transformed the field. Endovascular devices for neurointerventional procedures have been proliferating for many years. Debate concerning these techniques has focused on the distinction between clinical outcomes and vascular end points, such as the technical efficacy of arterial recanalization. The dissimilar regulatory processes for approval of drugs and devices have also received much attention. More subtle issues relate to the nature of these different therapeutic approaches. Devices may selectively target specific biophysical mechanisms and thereby enhance an endogenous pathophysiologic process, whereas drugs may exhibit more complex interactions.

Unlike drugs administered in a standard fashion, the efficacy of devices may depend on operator experience, as procedural variables may be difficult to ascertain. Devices have flourished in the growing competition to develop effective therapies for acute ischemic stroke. Current investigational device strategies include infrared laser therapy transmitted through the skull, stimulation of the sphenopalatine ganglion, and endovascular catheters for novel recanalization approaches, induction of hypothermia, and perfusion augmentation.

The concept of blood diversion due to vascular collapse as a mechanism of perifocal cerebral ischemia, and the possibility to abolish this diversion with increased venous pressure, has been previously described. However, this has never been applied to treat patients in whom venous steal is present, where blood, flowing in the path of least resistance, is diverted from areas where it is needed (e.g., in the immediate peristroke vicinity). Moreover, none of the existing methods for treatment of stroke or cerebral ischemia directly address enhancement of penumbral blood flow.

SUMMARY

Although previous approaches have emphasized pressure augmentation in arterial inflow routes providing collateral blood flow, the critical pathophysiology may actually involve downstream resistance of venous outflow pathways. Cerebral venous steal, or diversion of blood volume to the periphery of the ischemic territory, may thus occur caused by the collapsible nature of venous circuits in the brain. Such displacement of blood volume may lead to increasing downstream resistance due to focally collapsed veins once critical closing pressures are compromised. Conversely, increased blood volume and distension of cerebral veins may enhance tissue perfusion.

Accordingly, embodiments of the invention target ischemia rather than clot disruption or consideration of venous hemodynamics and flow redistribution. For acute and chronic treatment of stroke and other cerebral ischemia, embodiments of the invention use cerebral venous outflow modulation to abolish cerebral vessel collapse and venous steal, thereby increasing cerebral collateral and penumbral flow. The venous outflow modification method described herein may be used in combination with antegrade perfusion enhancement methods.

Accordingly, embodiments of the invention provide devices and methods for improving cerebral collateral perfusion in patients suffering from either local or global ischemia, in either the acute or chronic timeframes. In one embodiment, the apparatus comprises a catheter which includes an elongated tubular member having a proximal end, a distal end, and first and second lumens. The first lumen communicates with the proximal end and a port at the distal end of the catheter. The second lumen communicates with the proximal end of the catheter and a port proximal to the expandable occluder. An expandable occluder, which may be an elastomeric balloon in certain embodiments, is mounted on a distal region of the catheter between the proximal port and the distal port. A manometer, or other pressure measurement device, is mounted to the proximal end of the second lumen, which is located proximal to the occluder for measuring venous pressure proximal to the occluder.

Embodiments of the invention are capable of rapidly reestablishing collateral cerebral blood flow (cCBF) at a rate sufficient to relieve penumbral ischemia distal to the occlusion. The techniques described herein could be adaptable for use both in an emergency situation (e.g., outside the hospital), within a hospital environment, or even in an outpatient or chronic setting. To avoid reperfusion injury, embodiments of the invention may enable control over the rate of cCBF and/or cessation of cCBF to the ischemic region. In addition to treating ischemia, the embodiments of the invention may provide access and support for performing other therapeutic interventions to treat the ischemia, including drug interventions to treat stroke and to provide supportive therapy. Additionally, embodiments of the invention may use access routes that are familiar to most health care professionals, so as to permit rapid and wide spread adoption.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Overview of Pathophysiology

In accordance with embodiments of the invention, treatment of ischemia in the brain is achieved by the control of the collapsibility factor in the cerebral vasculature. It may therefore be deemed pertinent to review basic physiological effects, related to collapsibility of intracranial vessels, before discussing specific embodiments of the invention.

Cerebral vessels like other collapsible tubes tend to collapse when external pressure exceeds intravascular (negative transmural pressure). When intravascular pressure is increased (i.e., positive transmural pressure), vessels reopen and their diameter increases. It has been demonstrated that resistance in the collapsible vascular beds decreases when transmural pressure increases. Active wall tension also contributes to vessel collapse and results in critical closing pressure. Critical closure pressure is the inflow pressure at which flow through the vascular bed stops. Due to pressure drop through the feeding arteries and active autoregulation, intravascular pressure at the microcirculation is not directly related to systemic arterial pressure. However, it is directly proportional to the venous pressure. The dependence of intravascular pressure, resistance, and collapsibility on the venous pressure allows venous pressure to be used to modify perifocal blood vessel collapse and flow distribution. Increasing venous pressure may seem counterintuitive; however, this approach or mechanistic modification of the circulatory bed may actually augment cerebral blood flow and open collaterals circuits in penumbral regions that are at-risk for evolving infarction.

Experimental physiological data indicate that intracerebral vein pressure is slightly above intracranial pressure (ICP). However, dural sinus pressure is lower than that in the smaller veins and not related to ICP. Spontaneous increase in ICP does not affect jugular vein bulb pressure (JVBP). Similarly, a small JVBP increase does not affect ICP, although a more extensive increase of JVBP raises both cerebral venous pressure and ICP to an equal extent. If JVBP is low, its drop does not affect ICP or cerebral venous pressure. If JVBP is high, its drop affects ICP and cerebral venous pressure to an equal extent. This is caused by an interesting physiological phenomenon referred to as a "vascular waterfall." When this happens, flow rate through a collapsible tube will depend only on an upstream pressure at the feeding segment and will be independent of downstream pressure at the exit end. This behavior is similar to that of a mountain waterfall, where the flow rate depends on the quantity of flow at the source and not on the height of the vertical drop or fall. This is in a sharp contrast to ordinary laminar or turbulent flow in rigid pipes, where flow is simply proportional to the pressure gradient between the ends.

Analysis of vessel collapse shows that under some circumstances provision of resistance to the outflow end might actually enhance flow through a collapsed tube segment. This is because distal resistance increases distending pressure on the collapsed segment, which may eliminate the most effective hindrance to flow, progressive and recurrent narrowing of the collapsed segment. This is because collapsible tubes have an unequivocal and nonlinear flow (Q) pressure (P) interrelationship. When transmural pressure (Ptm) is positive, the cerebral veins assume a circular cross shape. If external pressures exceed venous pressure, the vein wall is subjected to circumferential compression with subsequential diminution of their cross-sectional area and full collapse. Between a fully-distended and fully-collapsed state, the cerebral veins exhibit a highly nonlinear and unequivocal P-Q interrelationship, part of which is inverted when veins are partially collapsed. In this part, flow through the vein increases as pressure gradient along it falls. In other words, it is possible to augment cerebral blood flow (CBF) by decreasing an extra-intracranial pressure gradient. This is a physiological basis for reestablishing CBF via the collateral circulation in the brain, in accordance with embodiments of the invention.

Device And Method

Figure 1:
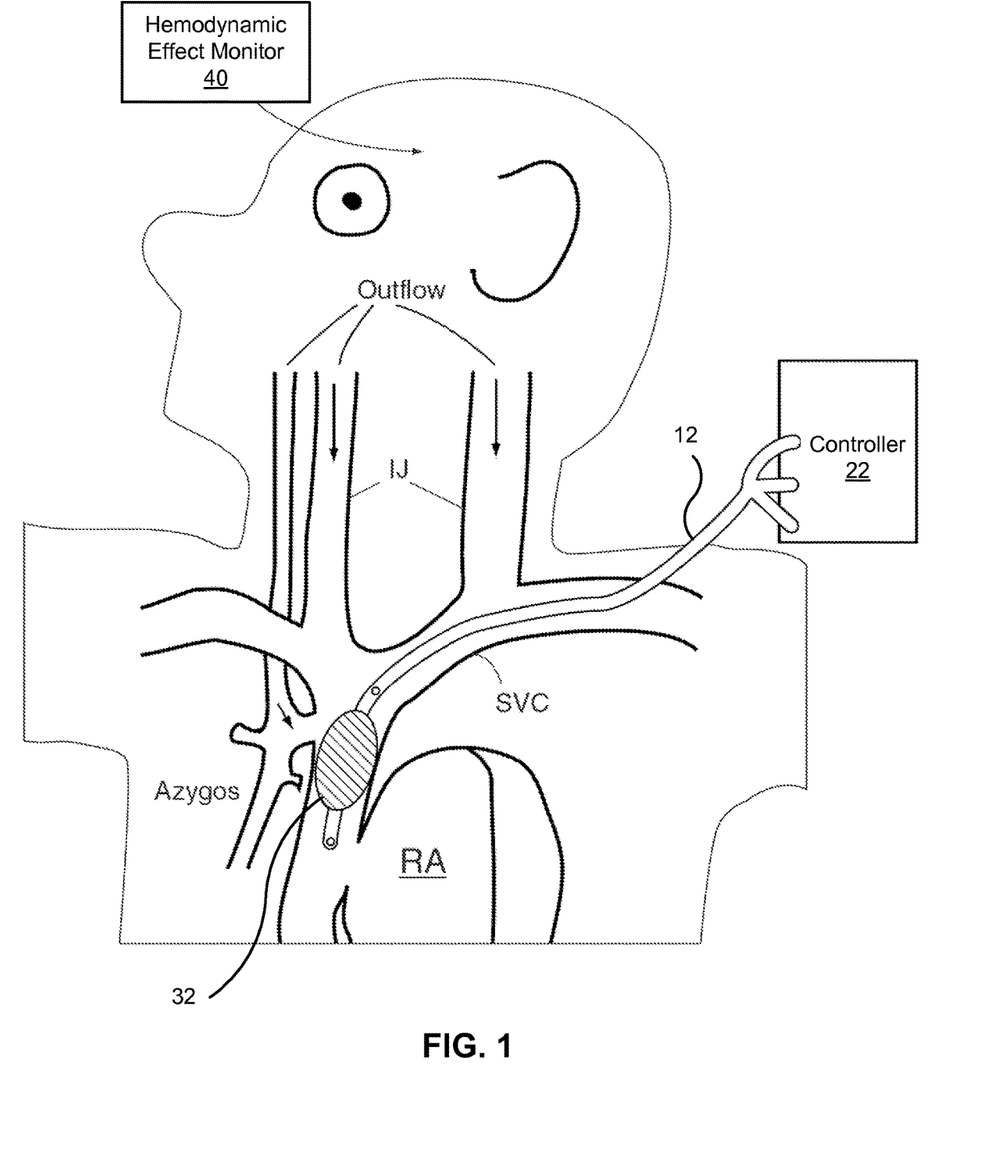
FIG. 1 is a diagram of a patient, and a portion of the patient's vascular system, being treated in accordance with an embodiment of the invention.

Accordingly, embodiments of the invention are used to treat a patient who is suffering from venous steal due to cerebral vessel collapse, which may otherwise lead to cerebral ischemia, by increasing the cerebral venous pressure in the patient. FIG. 1 is diagram of a patient illustrating a portion of the patient's vascular system, including interior the jugular veins (IJ), the superior venous cava (SVC), the right atrium (RA), and the azygos vein. FIG. 1 illustrates a oxygen demand directed technique for treating the patient.

As illustrated, distal end of an occluding catheter 12 is inserted through a percutaneously accessible vein, such as the jugular or subclavian vein, into the SVC. The distal region of the occluding catheter 12 contains an expandable balloon 32, or other expanding mechanism, which is positioned in the SVC at a location above the RA and below where the azygos vein connects to the SVC. The position of the occluding catheter 12 and balloon 32 may be confirmed, for example, via x-ray.

Once the occluding catheter 12 is in place, the balloon 32 is expanded to occlude blood flow in the SVC at least partially. The degree of occlusion in the SVC may be varied according to the venous pressure, which may be recorded by a pressure sensor that records pressure proximal to the balloon 32 or other portion of the occluding catheter 12. In addition, the occluding catheter 12 may include mechanisms to measure other physiological parameters. For example, flow may be measured by Doppler ultrasonography, electromagnetic flow meters, or heat dilution; and blood oxygenation may be measured by fiberoptic oximetry or concentration of metabolites or markers.

In addition, the patient may be connected to a hemodynamic effect monitor 40, which measures the cerebral blood flow in the patient's head. In this way, the hemodynamic effect monitor 40 provides feedback for whether and to what extent the treatment results in the desired increased cerebral blood flow. In one embodiment, the hemodynamic effect monitor 40 uses TCD waveforms to obtain a mapping of the patient's cerebral blood flow. In other embodiments, the hemodynamic effect may be monitored using spectrometry or CT angiography.

Figure 2:
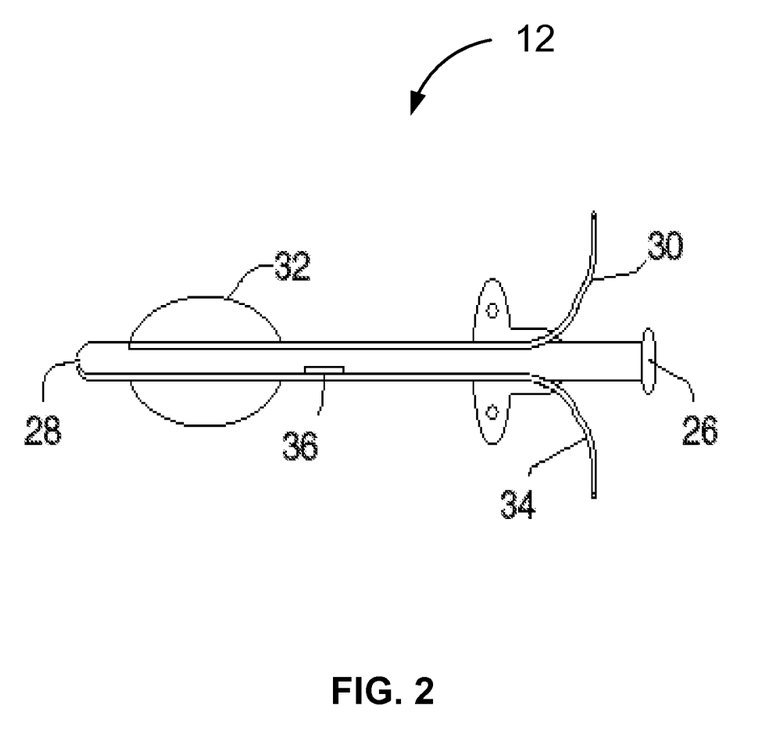
FIG. 2 is a diagram of a device for treating cerebral ischemia in accordance with an embodiment of the invention.

FIG. 2 is a diagram of the venous occlusion catheter 12, which may be used in connection with the embodiment illustrated in FIG. 1. The catheter 12 is of a length sufficient to extend from an insertion point to the SVC. The outer diameter of the catheter is less than the inner diameter of the SVC at a location whether the SVC is to be occluded. The catheter 12 is preferably opaque to X-rays and may be marked at the tip for easy visualization using conventional X-ray equipment.

In one embodiment, the catheter 12 comprises a main lumen 26 opening at the tip 28 of the catheter. The catheter further comprises a balloon lumen 30 that forms a low resistance connection between an inflatable balloon 32 and a pump, e.g., via a reservoir. The inflatable balloon 32 is preferably made from a highly compliant or easily folding material so that the balloon 32, the low resistance balloon channel 30, and the reservoir together form a high compliance system. This system may be filled with a low viscosity gas, such as helium.

The catheter 12 may incorporate a conventional optic fiber 34 to allow for oxygen saturation measurement in the SVC. The catheter 12 may further incorporate a thermistor 36, positioned close to the catheter tip 28 and proximally to the balloon 32 for cerebral blood flow (CBF) measurement. The main lumen 26 of the catheter 12 is coupled to the controller 22 for pressure sensing of the SVC. Alternatively the SVC pressure can be sensed through a conventional fiberoptic pressure sensor in the catheter 12. The main catheter lumen 26 is also connected to a pump for fluid injection/withdrawal to actuate the balloon 32.

Figure 3:
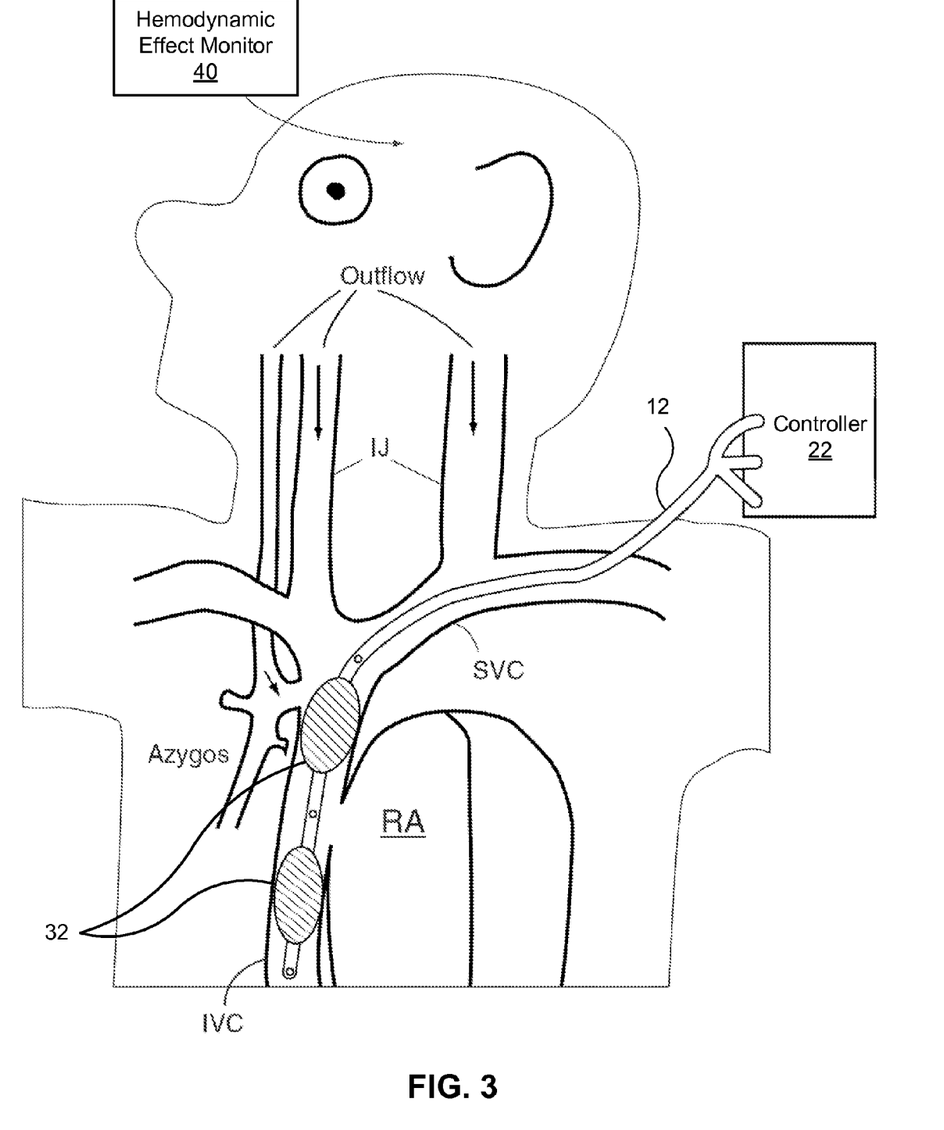
FIG. 3 is a diagram of a patient, and a portion of the patient's vascular system, being treated in accordance with another embodiment of the invention.

In another embodiment for treating venous steal due to cerebral vessel collapse, illustrated in FIG. 3, the occluding catheter 12 may comprise a plurality of expandable balloons 32, each coupled to controller 22 and individually expandable. In operation, a lower balloon 32 may be positioned between the RA and the inferior venal cava (IVC), and the upper balloon 32 positioned between the RA and the SVC. This embodiment allows control of flow from the IVC while the outflow in the SVC is being occluded. Using this dual balloon embodiment, an operator may alternatively or simultaneously occlude only the jugular vein or the jugular with the azygos veins (which collects blood from the vertebral plexus). This allows for improved control; otherwise, the azygos vein outflow can be controlled only with hydrostatic pressure (e.g., by placing the patient's head down).

In another embodiment for treating venous steal due to cerebral vessel collapse, cerebral venous pressure increase is achieved by occluding one or both of the internal jugular veins. This may be achieved, for example, by inserting the distal end of an occluding catheter 12 in the right or the left internal jugular vein. In such an embodiment, the occluding catheter 12 is modified to fit within the structure of the interior jugular vein. A balloon 32 of the occluding catheter 12 is expanded within the jugular vein to occlude the return flow from the brain to the heart. As with occluding flow in the SVC, this may also increase the cerebral venous pressure and thereby restore collapsed cerebral veins to increase the cerebral blood flow therethrough. Advancing jugular catheter into the intracranial portion of venous circulation (e.g., the sigmoid sinus or straight sinus) allows venous pressure control in the selective part of cerebral venous circulation. In another embodiment, cerebral venous pressure increase can be achieved by inserting the distal ends of an occluding catheter 12 in each of the right and the left internal jugular veins.

Figure 4:
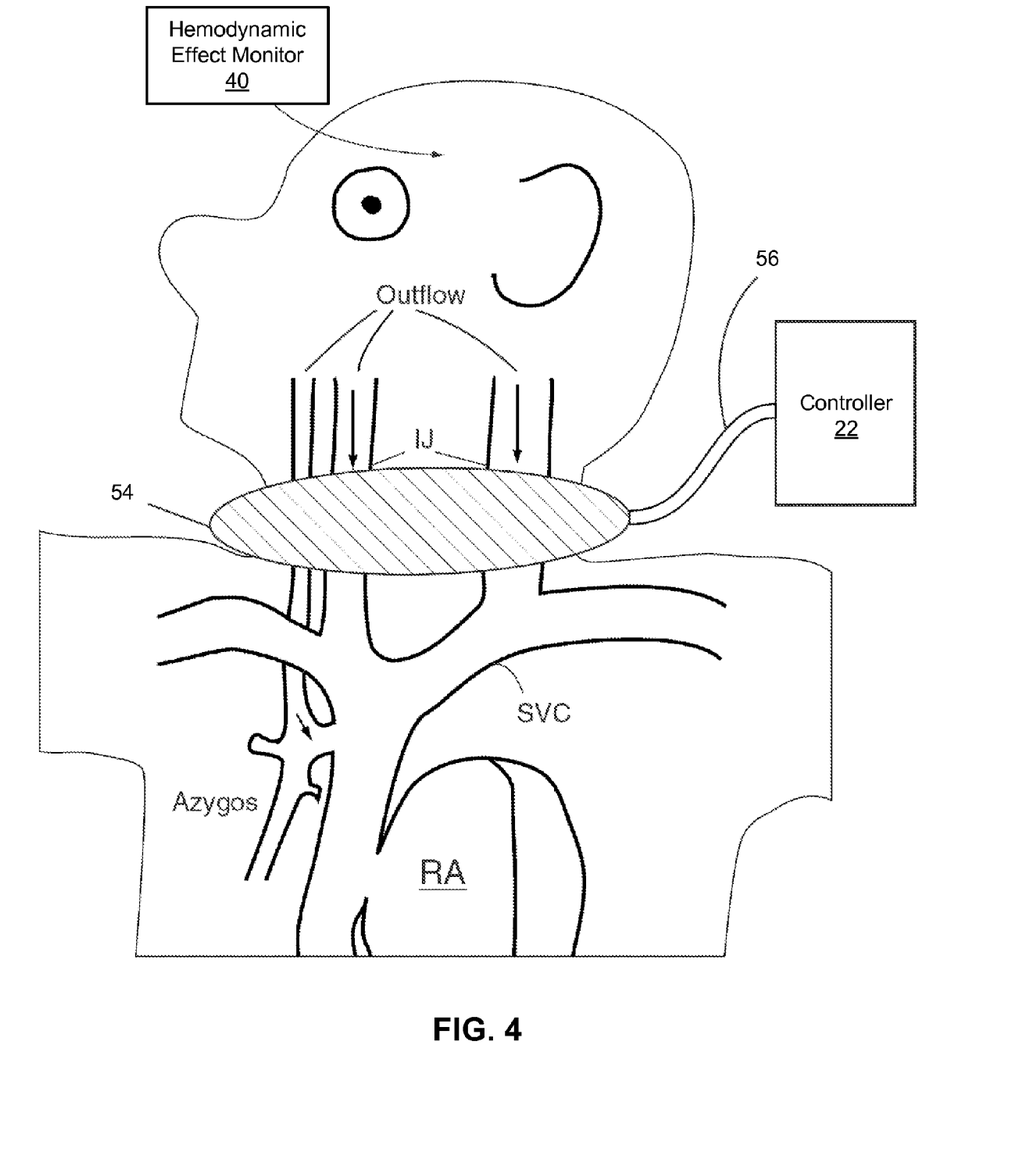
FIG. 4 is a diagram of a patient, and a portion of the patient's vascular system, being treated in accordance with another embodiment of the invention.

FIG. 4 illustrates another embodiment in which cervical vein occlusion is achieved with external cervical compression device. In this embodiment, a cervical cuff 54 is placed around a patient's neck, where the cervical cuff 54 is coupled to the controller 22 via a hose 56. The controller 22 may include a pump to actuate the cervical cuff 54 via the hose 56, causing the cervical cuff 54 to tighter around the patient's neck and partially occlude the cervical veins. In this way, increased cerebral venous pressure can be achieved quickly and without any invasive procedure.

There are several advantages in using the various embodiments of the devices and methods disclosed herein for protecting the brain and cerebral vasculature of patients suffering from global or local ischemia due to venous steal. For example, compared with known techniques for retrograde cerebral venous perfusion, the retrograde venous perfusion of the invention (1) does not produce backflow of blood to the brain, thereby eliminating retroperfusion injury; (2) eliminates the need for IVC clamping, thereby avoiding damage to the IVC; (3) provides an accurate measurement of the jugular venous pressure; (4) is very easy to administer (akin to placement of central venous catheters that most physicians learn during early training stages) so does not require specialized medical personnel; (5) is expected to have very low complication rates due to its simplicity; and (6) can be combined with IVC catheterization procedures for administration of fluids, drugs, and the like.

In one embodiment, the degree of vessel occlusion may be controlled by a balloon inflator (e.g., a pump) in the controller 22, which can be manually or automatically controlled. Balloon inflation is preferably limited to a value of pressure and/or volume selected as maximal safe level (P_balloon_max and/or V_balloon_max). Once the balloon is maximally inflated, a before and after balloon pressure gradient (dPmax) is measured. The balloon is then gradually deflated until dP diminishes. The level of balloon inflation that maintains dP near dPmax is P_balloon_submax. In one embodiment, this pressure is selected as the optimal inflation pressure at which to maintain the occluding catheter 12 during treatment of the patient.

In one embodiment, the expandable balloon may have a large-volume, high-compliance design with or without a fixed pressure external inflation reservoir. This embodiment allows a fixed-pressure, variable-volume balloon inflation. Fixed balloon pressure limits dP increase to P_balloon.

In one embodiment of the treatment procedure, a patient is initially selected who is experiencing an acute onset of neurological deterioration due to stroke or cerebral ischemia, cause by venous steal. The patient is screened for an ability to modify cerebral blood flow or collateral flow augmentation by trendelenburg/valsalva.

Once the patient is determined to be a candidate for the procedure, the occluding catheter 12 is inserted into the patient's venous system and positioned in the body as desired. In position, the balloon 32 of the occluding catheter 12 is inflated, using for example the controller 22. (Alternatively, occlusion may be achieved externally using the cervical cuff 54, shown in FIG. 4.) The venous pressure is measured using the catheter 12, and the cerebral blood flow response is assessed using the hemodynamic effect monitor 40, which data may be provided to the controller 22. Responsive to the venous pressure and cerebral blood flow measurements, the occlusion of the catheter 12 is modulated to achieve an optimal response (e.g., maximal cerebral blood flow). This therapy is continued until the patient's condition improves, or for a predetermined time period. Beneficially, the improvement in the patient's condition is expected to have a persistent effect even after treatment is ceased, since the increased cerebral blood flow will tend to keep the cerebral venous structure from collapsing without need for continued increased venous pressure.

In one embodiment, the following control algorithm is used to determine the optimal occlusion by the occluding catheter 12. This algorithm optimizes regional cerebral blood flow (CBF) by increasing venous pressure via occlusion, responsive to the measured venous pressure and CBF. The steps of the algorithm are:

1. Obtain baseline CBF(t0), map rCBF(t0), collateral flow(t0)
2. Obtain baseline MAP(t0), CVP(t0)
3. Calculate CPP(t0)=MAP(t0)−CVP(t0)
4. Change CVP by DPv(t0+dt)
5. Map rCBF response to DPv:
    a. ohms response (rCBF reduction proportional to CPP reduction): d(rCBF)=(CBF(t0)−0)/CPP(t0)−Dpv)
    b. Starling response (rCBF=const or changes little)— characteristic for the large regions with increased tissue pressure or when CBF autoregulation is preserved (CBF independent of CPP): d(rCBF)<(CBF(t0)−0)/CPP(t0)−Dpv); or d(rCBF)=0
    c. steal response—rCBF increases while CPP decreases—characteristic for heterogenous perifocal regions with rCBF diversion
6. Determine from rCBF mapping (step 1) regions with critically reduced rCBF (at risk for permanent injury)
7. Determine from the step 5 whether critical regions have steal response (5c)
8. Elevate CVP to the level where rCBF5c (steal) is maximized and exceeds critical flow threshold, while rCBF5a (ohm's response) decreases, but stays above the ischaemic threshold
9. Reassess rCBF response to CVP periodically
10. Result: optimized rCBF distribution with the decreased chance of permanent ischaemic injury in perifocal regions Summary The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like.

As used herein, the term "proximal" refers to a position closer to the catheter end outside the body and venous circulation part away from the heart. If the catheter is inserted so that is distal part is closer to the brain (e.g., inserted via inferior vena cava), the terms "proximal" and "distal" still apply to the catheter, but when referred to the venous system they refer to the part closer to the brain (i.e., proximal) or closer to the heart (i.e., distal). Usage of the lumens is reversed in the latter case.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method for treating cerebral ischemia in a patient, the method comprising:
    selecting a patient in whom blood diversion due to cerebral venous steal is present and abolishment of the cerebral venous steal is indicated, the cerebral venous steal caused by focally collapsed cerebral vasculature;
    placing a cervical cuff externally around the patients neck;
    increasing a cerebral venous pressure in the patient by inflating the cervical cuff and thereby occluding one or more veins coupled to the collapsed cerebral vasculature; and
    adjusting inflation of the cervical cuff to an optimal occlusion level using parameters comprising cerebral blood flow (CBF), central venous pressure (CVP), cerebral perfusion pressure (CPP) and mean arterial pressure (MAP) at which regional cerebral blood flow (CBF) is optimized; and maintaining the increased cerebral venous pressure at the optimal occlusion level for a period of time sufficient to restore at least a portion of the patient's collapsed cerebral vasculature and thereby treating the patient for cerebral ischemia.

2. The method of claim 1, wherein the patient is suffering or has suffered from a stroke.

3. The method of claim 1, wherein the one or more veins comprise a portion of the patients superior vena cava.

4. The method of claim 1, wherein the one or more veins comprise a portion of the patients superior vena cava between the patient's right aorta and azygos vein.

5. The method of claim 1, wherein the one or more veins comprise one or both of a patients interior jugular veins.

6. The method of claim 1, wherein the method is non-invasive.

7. The method of claim 1, further comprising:
mapping the cerebral blood flow and the venous pressure non-invasively while the increased cerebral venous pressure is being maintained; and
adjusting the increased venous pressure as a function of at least the cerebral blood flow non-invasively.

8. The method of claim 7, wherein the increased venous pressure is adjusted until the optimal occlusion level is obtained.

9. The method of claim 7, wherein the cerebral blood flow is mapped using transcranial doppler (TCD) waveforms.

10. The method of claim 1, wherein cerebral blood flow heterogeneity and blood flow in ischemic areas of the patient's brain are maintained above the critical ischemic threshold.

11. The method of claim 1, further comprising removing the occlusion cervical cuff from the one or more veins coupled to the collapsed cerebral vasculature.

12. The method of claim 1, further comprising measuring venous pressure and regional cerebral blood flow (CBF) while the one or more veins are occluded.

13. The method of claim 12, wherein the one or more veins comprise the patient's cervical veins.

14. The method of claim 12, wherein the CBF is measured by applying transcranial doppler (TCD) waveforms.

15. The method of claim 12, further comprising maintaining cerebral blood flow heterogeneity and blood flow in ischemic areas of the patient's brain above a critical ischemic threshold.

* * * * *

UNITED STATES PATENT AND TRADEMARK OFFICE
CERTIFICATE OF CORRECTION

PATENT NO. : 9,833,598 B2  
APPLICATION NO. : 14/220020  
DATED : December 5, 2017  
INVENTOR(S) : David S. Liebeskind et al.

Page 1 of 1

It is certified that error appears in the above-identified patent and that said Letters Patent is hereby corrected as shown below:

On the Title Page

Under abstract, "15 Claims, 4 Drawing Sheets" should read --19 Claims, 4 Drawing Sheets--.

In the Specification

Column 8, Line 60, the word "patients" should be changed to --patient's--.

Column 10, Line 11, after "the" delete "occlusion".

In the Claims

Column 10, Line 24, insert the following missing claims:

--16. The method of claim 1, wherein the patient is suffering or has suffered from a stroke and the method is non-invasive.

17. The method of claim 1, wherein the one or more veins comprise a portion of the patient's superior vena cava and the method is non-invasive.

18. The method of claim 1, wherein the one or more veins comprise a portion of the patient's superior vena cava between the patient's right aorta and azygos vein and the method is non-invasive.

19. The method of claim 1, wherein the one or more veins comprise one or both of a patient's interior jugular veins and the method is non-invasive.--.

Signed and Sealed this  
Twenty-seventh Day of August, 2019

Andrei Iancu  
*Director of the United States Patent and Trademark Office*